United States Patent [19]
Copf et al.

[11] Patent Number: 5,776,202
[45] Date of Patent: Jul. 7, 1998

[54] JOINT PROSTHESIS

[76] Inventors: Franz Copf, Marienstr. 12, D-70178 Stuttgart; Gunter Rentsch, Hohestr. 5, D-70174 Stuttgart; Peter Reill, Schnarrenbergstr. 95, D-72076 Tübingen, all of Germany; Srecko Herman, Mekinceva 11, SI-6100 Lubljana, Slovenia

[21] Appl. No.: 605,168

[22] PCT Filed: Sep. 7, 1994

[86] PCT No.: PCT/EP94/02977

§ 371 Date: Sep. 18, 1996

§ 102(e) Date: Sep. 18, 1996

[87] PCT Pub. No.: WO95/07060

PCT Pub. Date: Mar. 16, 1995

[30] Foreign Application Priority Data

Sep. 7, 1993 [DE] Germany ................ 43 30 248.3

[51] Int. Cl.⁶ .................................................. A61F 2/42
[52] U.S. Cl. .................................... 623/21; 623/18
[58] Field of Search ........................ 623/21, 20, 18

[56] References Cited

U.S. PATENT DOCUMENTS

| | | | |
|---|---|---|---|
| Re. 34,632 | 6/1994 | Berggren et al. | |
| 3,899,796 | 8/1975 | Bahler et al. | |
| 4,064,568 | 12/1977 | Grundei et al. | |
| 4,156,296 | 5/1979 | Johnson | 623/21 |
| 4,204,284 | 5/1980 | Koeneman | |
| 4,375,703 | 3/1983 | Evans | 623/21 |
| 4,725,280 | 2/1988 | Laure | 623/21 |
| 4,936,859 | 6/1990 | Morscher et al. | |
| 4,955,916 | 9/1990 | Carignan | 632/23 |
| 5,002,579 | 3/1991 | Copf | 623/23 |
| 5,032,129 | 7/1991 | Kurze | 623/23 |
| 5,047,059 | 9/1991 | Saffar | 623/21 |
| 5,061,288 | 10/1991 | Berggren et al. | |
| 5,147,386 | 9/1992 | Carignan et al. | |
| 5,314,486 | 5/1994 | Zang et al. | |
| 5,534,033 | 7/1996 | Simpson | 623/21 |
| 5,549,681 | 8/1996 | Segmüller | 623/21 |

FOREIGN PATENT DOCUMENTS

| | | | |
|---|---|---|---|
| 0245846 | 11/1987 | European Pat. Off. | |
| 0328848 | 8/1989 | European Pat. Off. | |
| 2425237 | 12/1979 | France | |
| 2605878 | 5/1988 | France | 623/21 |
| 2338137 | 1/1975 | Germany | |
| 2839150 | 3/1980 | Germany | |
| 3536895 | 5/1986 | Germany | |
| 3613657 | 11/1987 | Germany | |
| 2056862 | 3/1981 | United Kingdom | |
| WO 8906946 | 8/1989 | WIPO | |
| WO 9300053 | 1/1993 | WIPO | |

*Primary Examiner*—Michael J. Milano
*Attorney, Agent, or Firm*—Dinsmore & Shohl LLP

[57] ABSTRACT

A joint prothesis, which is suitable for small joints and can be implanted without using a cement, comprises two prothesis members (12, 14), each having a joint element (20, 22) made from from PE as well as an anchoring unit (16, 18) cast from titan. The anchoring unit (16, 18) each have a mounting plate (28) and at least one anchoring element (38) carried by the latter, which includes a core portion (40) and anchoring disks (42) carried by the latter. At least an end portion of the anchoring elements (38) is elastically and/or plastically deformable thus enabling the enchoring elements to conform to the contour of a cavity cut into a bone.

41 Claims, 5 Drawing Sheets

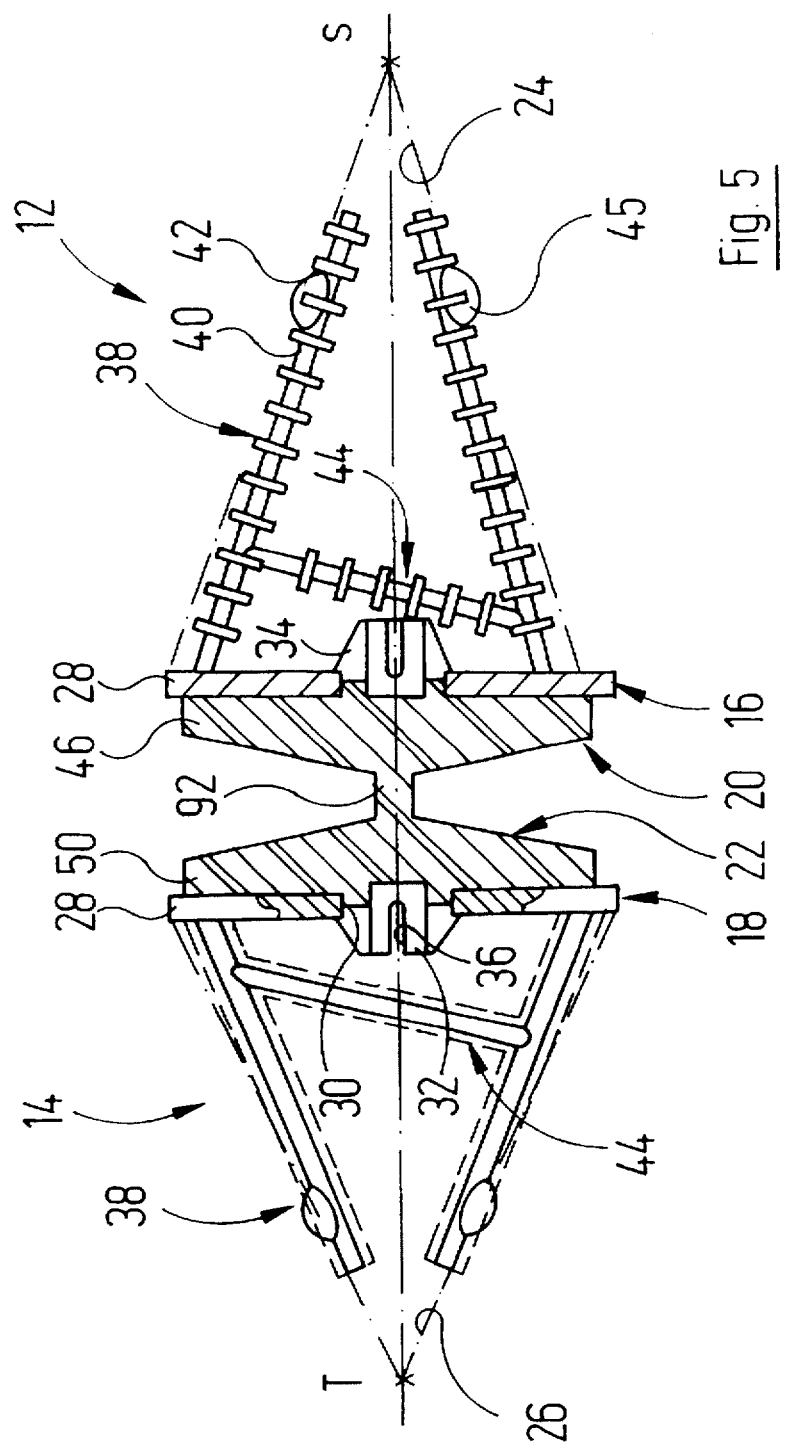

JOINT PROSTHESIS

Such a joint prosthesis is disclosed in EP 0 245 846 B1. Actually such known prostheses are used for hip joints.

In contrast thereto in connection with small joints like finger joints or toe joints shaft prostheses are actually used exclusively. which are cemented into the ends of the finger and toe bones, respectively, after the old joint has been resected, the cement used being a plastics material based cement. Such cemented joint prosthesis for small joints are of comparatively low working life, since the shafts of the prosthesis members will detach from the walls of the bones.

It is thus an object of the present invention to provide a joint prosthesis of the kind described above being improved in that it is suited for use in small joints like finger joints and toe joints.

In accordance with the invention this object is solved by a joint prosthesis of the present invention.

In the bones of the hand and the foot, which are of small dimension. only, as compared to the thigh bones and pelvic bones, there is only a comparatively small usable volume of spongiosa. The inventors found out that nevertheless cementless implantation of a prosthesis member into these tube bones can be obtained. if provisions are made warranting that the different anchoring elements are located close to the hard corticalis. Thus tilting moments exerted onto the anchoring unit can be well taken up and a large free space is available for the spongiosa to form a stable spongiosa structure after regeneration. In order to allow for such an arrangement of the prosthesis member inspite of the individual bone geometries changing from one person to another. in accordance with the present invention it is suggested to form the anchoring elements at least in the end portions thereof as elastically or plastically deformable members. Thus an anchoring unit will automatically conform to a bone which is to receive a prosthesis member, it being understood, that large dimensional differences are taken account of by providing anchoring units of different size, as is customary in connection with prostheses.

The further improvement of the invention provides for long flectional portions of the anchoring elements and independence of the deformations the anchoring elements undergo in conforming to the respective geometry of the bone.

In accordance with the present invention the stiffness of the anchoring elements may be increased in the immediate neighbourhood of the mounting plate and additional anchoring surfaces defined between the spongiosa and the anchoring unit may be provided in that space, where the spongiosa filled volume of the bone has still noticeable dimensions.

In a joint prosthesis of the present invention the anchoring unit has a particularly simple geometry. The anchoring unit can thus be produced at particularly low cost.

In connection therewith the further improvement of the invention results in the fact that the contact surfaces, through which the anchoring unit and the spongiosa material locally cooperate, are comparatively small. Thus a local stimulation of the spongiosa is obtained, which is advantageous in good blood circulation and continuous good regeneration.

The further improvement of the invention is also advantageous in view of good geometric adjustment of the anchoring unit to the actual bone geometry.

If a joint prosthesis is formed in accordance with the present invention, there is a large number of small contact surfaces between the anchoring unit and the spongiosa material, which is advantageous in view of good anchoring and good dynamic regeneration of the spongiosa.

In this connection the further improvement of the invention is advantageous in view of ease of production of the casting molds for producing the anchoring units and in view of ease of insertion of the anchoring unit into the emptied end portion of the bone.

The further improvement of the invention warrants homogeneous transfer of forces into the different portions of the spongiosa material. In addition the various secondary anchoring elements also form a cage type structure, which can somewhat retain ground spongiosa material, when the latter is filled into the anchoring unit and is introduced into the emptied end portion of the bone.

The further improvement of the invention will result in an even more homogeneous distribution of the transfer of forces into the spongiosa.

The further improvement of the invention warrants that the anchoring units are provisionally retained in the emptied end portion of the bone after insertion thereof under slight press fit conditions, which facilitates the work of the surgeon.

In connection therewith the improvement warrants that insertion of the prosthesis member under elastic and/or plastic deformation of the anchoring elements can be effected without exerting large forces and without the anchoring disks getting caught by engagement with the corticalis.

In accordance with the present invention, if additional convex integral contacting members are provided, the rest of the anchoring elements may throughout be formed as a cylindrical core carrying anchoring disks.

In a joint prosthesis in accordance with the present invention portions of the anchoring elements, which are not formed with anchoring disks radially projecting beyond the desired contour surface, also provide contact surfaces, through which the anchoring unit contacts the corticalis.

In view of obtaining an anchoring effect in the spongiosa also in the portions of the anchoring elements being adjacent to the contact surfaces, anchoring disks can be provided at these portions.

The dimensions of the anchoring disks and the cores of the anchoring elements, are advantageous in view of sufficient stimulation of the spongiosa by the loads experienced in every day use of the joint on one hand and in view of avoiding unduly large loads of the spongiosa.

The further improvement of the invention is advantageous in view of ease of mounting the joint elements made from plastics material on the metal made mounting plates.

In a joint prosthesis of the present invention, there is a positive limiting of the angle of rotation of the two axis ball type joint in arbitrary working directions. By providing a contoured edge portion of the abutment disk it is easy to define different angular limitations and different abutment effects for different working directions, if desired.

This angular limitation is obtained in elastic manner in a prosthesis in accordance with the present invention. The further improvement in accordance with a further parameter for modeling the resilient abutment effect, which is the dimension of the radial slots, which can be varied in addition to the thickness of the cantilever edge portion.

A prosthesis member in accordance with the present invention is particularly suited for use in such joints, which are exposed to tensional loads, too. Such a joint including joint elements which can be moved with respect to one another in the direction of the joint axis, after implantation is a good imitation of a natural joint also in that upon tensional loads the ligaments surrounding the joint are subject to load before the transfer of load is progressively and eventually mainly effected by the joint elements.

In accordance with the present invention one can allow in such a primarily one axis joint for an additional small tilting capacity in a direction being perpendicular to the main axis.

Below the invention will be described in more detail by way of preferred embodiments thereof referring to the drawings. Therein FIG. 1 is a longitudinal section through a first joint prosthesis for use with finger or toe joints;

Figure 2:
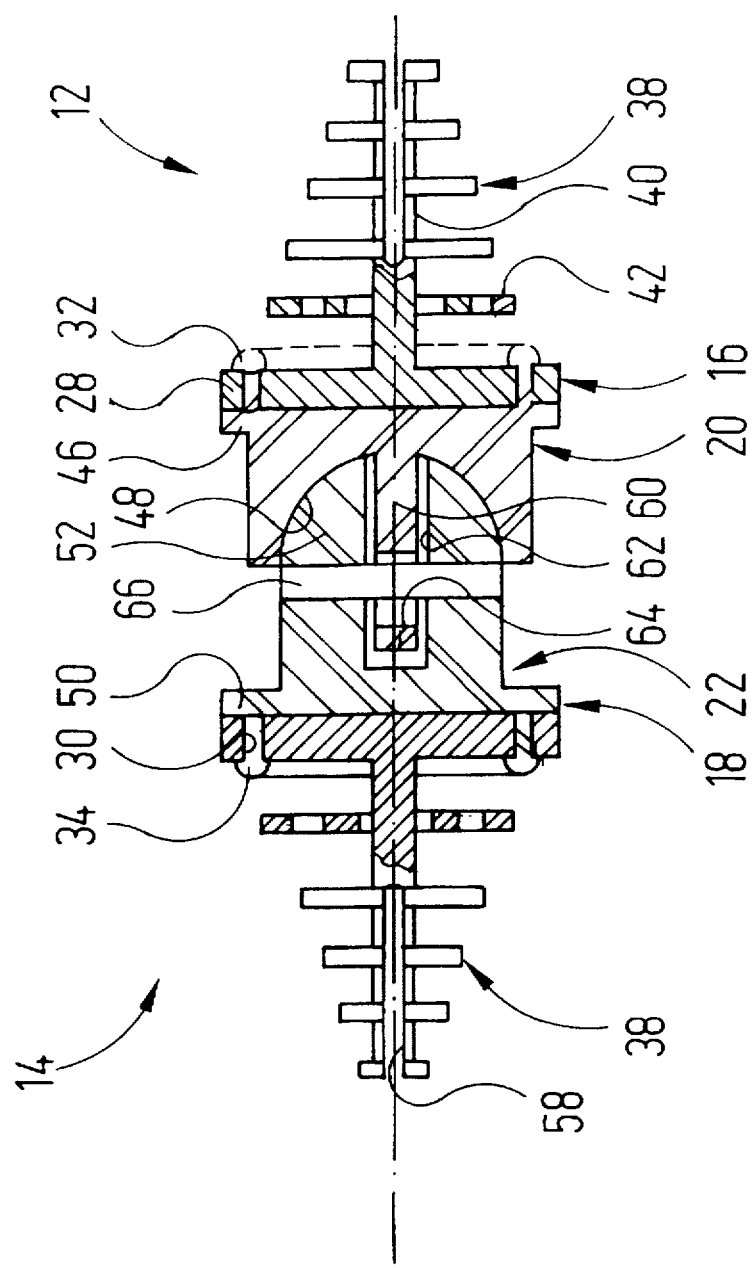
FIG. 2 is a longitudinal section through a second joint prosthesis for small joints.
Figure 4:
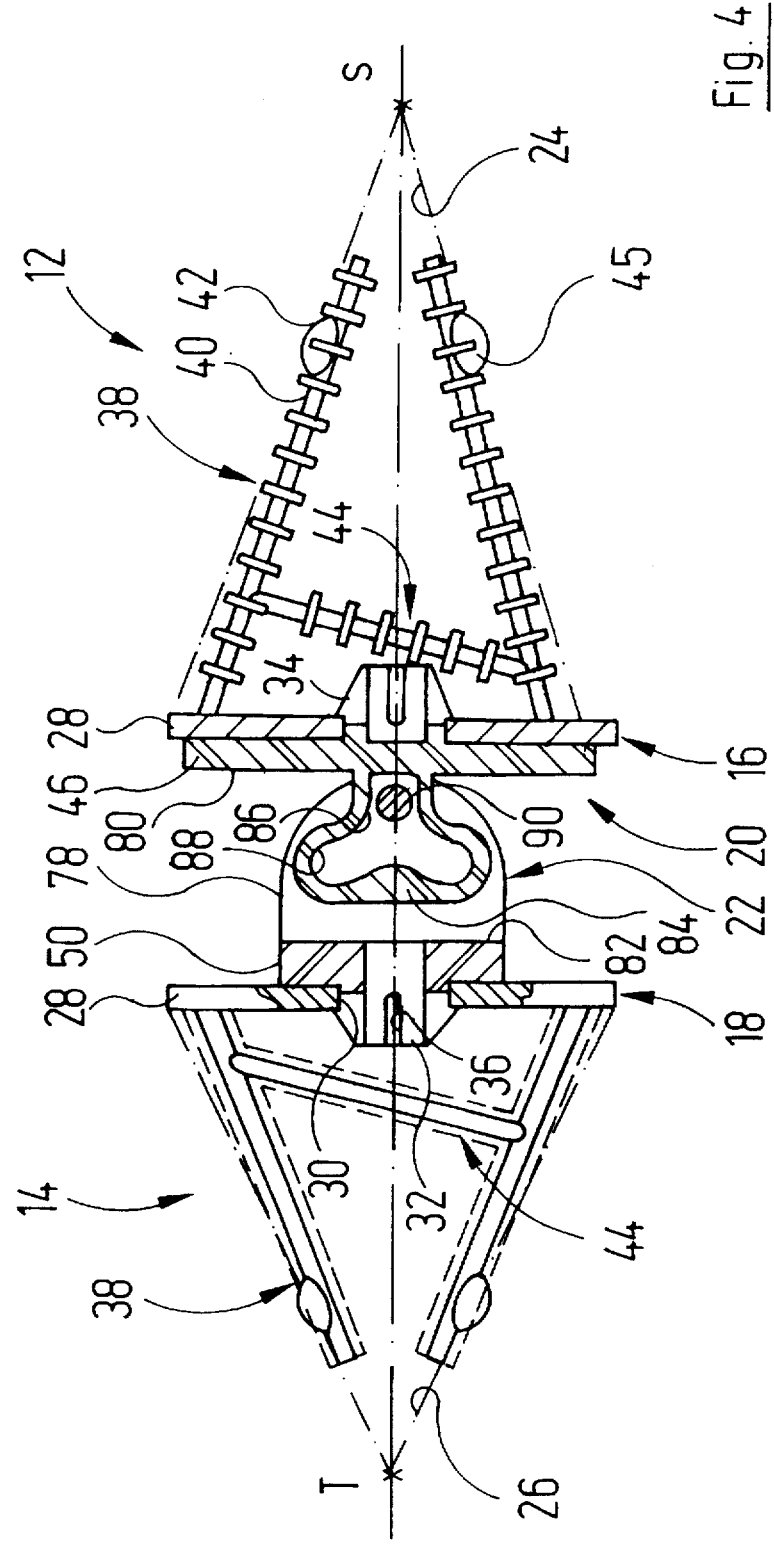

FIG. 4 a view similar to FIG. 2, wherein a joint prosthesis including a roll contact joint is shown; and FIG. 5 is an axial section through a still further modified joint prosthesis comprising a flectional joint.

Figure 1:
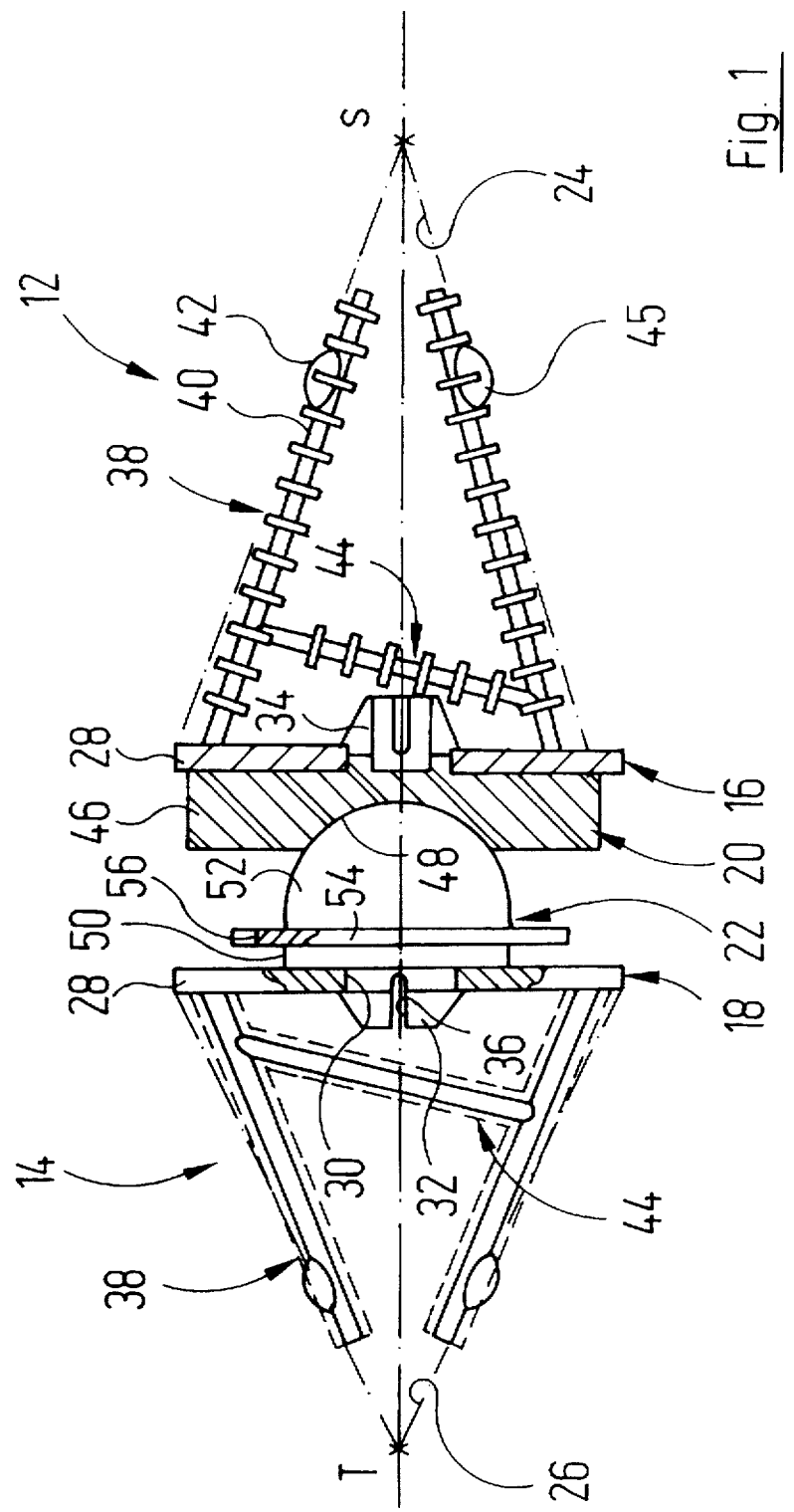

FIG. 1 shows a joint prosthesis for use in a metacarpus finger joint consisting of two prosthesis members generally shown at 12 and 14, respectively. The prosthesis members 12, 14 each consist of a anchoring unit 16 and 18, respectively, as well as a joint element 20 and 22 connected thereto by snap action. The anchoring units 16, 18 are of essentially same structure and show only small differences of their geometry, which conforms to the respective bone end portion, wherein the prosthesis member of interest is to be implanted. For the purposes of the present description it is assumed that in each of the end portions of the bone an essentially conical cavity is produced by removing spongiosa material. The idealized surfaces of these cavities are shown at 24 and 26, respectively, by dot-dash lines. For the purpose of the description it is assumed that the free ends of the cavities 24, 26 are of essentially equal diameter, that the cavities differ, however, as to their depth (location of the cone apex S and T, respectively).

The anchoring unit 16, 18 each have a mounting plate 28 being formed with a central opening 30 through which a mounting pin 32 and 34 of the associated joint element 20, 22 may be inserted under elastic compression, respectively. As may be seen from the drawings, the mounting pins 32, 34 each are formed with a plurality of circumferentially spaced axial slots 36 and their portion projecting from the back side (side, which is remote from the joint) of the mounting plate 28 is of conical shape, an outermost edge portion of the cone radially projecting beyond the edge of the opening 30.

A plurality of rod shaped anchoring elements 38 is cast integral with the mounting plates 28, respectively, each having a rod shaped core portion 40 and axially spaced anchoring disk 42 arranged thereon. In practical embodiments the core portions 40 have a diameter of about 0.8–1.5 mm, the anchoring disks 42 have a diameter being larger than the diameter of the core portions 40 by about 0.6–1.5 mm. The axial distance between the anchoring disks 42 in pratical embodiments is chosen to be about 2–4 mm, their thickness amounting to about 0.6–1.2 mm.

In the embodiment shown four anchoring elements 38 are provided, the base points of which essentially define a rectangle (in the case of an oval cross section of the bone). Portions of the anchoring elements 38 being adjacent to the mounting plate 28 are interconnected by stiffening elements 44, which in turn also comprise a core portion and anchoring disks carried thereby as has already been described in connection with the anchoring elements 38. In the embodiment considered here only two of the anchoring elements 38 are interconnected by stiffening elements 44, respectively. In a modified embodiment one may additionally provide stiffening elements extending perpendicular to the plane of projection of FIG. 1, if it is desired to reinforce the anchoring unit in the vicinity of the mounting plate 28 in this direction, too.

In the vicinity of the free ends of the anchoring elements 38 the exterior surfaces thereof have integrally cast lens shaped convex contact members 45, the exterior convex portions of which project beyond the anchoring disks 42 and thus allow easy pushing of the anchoring unit over the bone wall, which is left after emptying of the bone, without the anchoring disks being caught by the bone wall, which would require that chips must be severed from the wall to enable further progressing of the anchoring elements, since the surfaces of the cavities 24 and 26 partially extend radially inwardly of the exterior contour of the associated anchoring unit 16 and 18, respectively, as may be seen from the drawings.

The anchoring units 16, 18 are one piece members cast from a histocompatible member or a histocompatible alloy. Preferably the anchoring units 16, 18 are cast titanium parts.

The joint elements 20, 22 are injection molded parts made from histocompatible material, particularly polyethylene. The joint element 20 has a base plate 46 carrying the mounting pin 32, in which base plate a spherical joint socket 48 is formed. The joint element 22 comprises a base plate 50, the back side of which carries the mounting pin 34 and the front side of which carries a spherical joint ball 52. Close to the base of the joint ball 52 a radially projecting abutment disk 54 is formed integral with the joint ball 52, a peripheral portion of which may be additionally provided with radial slots 56 in view of reducing the spring action inherent to the abutment disk 54 due to the choice of material and due to the thickness of the disk in the outermost peripheral portion thereof.

As may be seen from FIG. 1, the mounting plate 28 of the anchoring unit 16 is not aligned exactly perpendicular to the axis of the prosthesis member but is tilted from the exactly transversal orientation by a small angle w. This is advantageous for use as a metacarpus finger joint.

Once the prosthesis has been implanted, the mounting plates 28 of the prosthesis members 12, 14 are flush with the ends of the bones to be interconnected, i.e. the corticalis of the end portion of the bone, which has been emptied and thereafter filled with ground bone material, overlies the circumferential surfaces of the mounting plates extending up to the end face of the mounting plate.

In the modified joint prosthesis shown in FIG. 2 components of the prosthesis functionally corresponding to prosthesis components, which have already been desribed referring to FIG. 1, have again the same numerals affixed thereto.

In this embodiment only a single anchoring element 38 is centrally formed integral with the mounting plates 28, which anchoring element has a larger diameter and carries a plurality of larger diameter anchoring disks 42. The anchoring disks 42 each have a grid structure, the webs of the grid being chosen such that in use of the joint a load per surface unit of the spongiosa material is obtained which is comparable to the load per surface unit obtained in the anchoring units shown in FIG. 1.

The axially outward portions of the anchoring elements 38 and the anchoring disks 42 are formed with four circumferentially spaced slots 58 so that the sectors of the anchoring disks 42 are adapted to independently elastically move in radial inward direction.

The joint elements 20, 22 now are connected to the associated mounting plates 28 by means of a plurality of mounting pins 32, 34 arranged at the rim of the mounting plate and being distributed in circumferential direction. Before assembly the mounting pins 32, 34 are of simple rod shape; their head portions have been obtained by heating and shaping of the thermoplastic material, after the joint elements have been fit onto the mounting plate.

A further modification of the prosthesis as compared to the one shown in FIG. 1 is the fact that the joint is formed as an essentially uniaxial joint, i.e. the cooperating journalling surfaces of the joint socket 48 and the joint ball 52 are cylindrical surfaces. A land 60 is projecting from the joint socket 48 engaging into a slot 62 formed in the joint ball 52 under lateral play. The land 60 is provided with an elongated opening 64, through which a pin 66 extends, which in turn is fixed in the joint ball 52.

In the joint shown in FIG. 2 the journalling surfaces of the joint socket and the joint ball cooperate only, when the joint experiences a compressional load. If a tensional load is exerted onto the joint, the two journalling surfaces are separated due to the connection formed by the elongated opening 64 and the pin 66, and transfer of the load from the joint element 22 to the joint element 20 is via the connection formed by the pin and the elongated opening. When exposed to tensional loads, the joint element 22, furthermore, can be slightly tilted with respect to the joint element 20 in a direction being perpendicular to the main axis of the joint to an extent being given by the clearance defined between the land 60 and the slot 62. Such a joint is particularly suited for use as a metacarpus finger joint.

Figure 3:
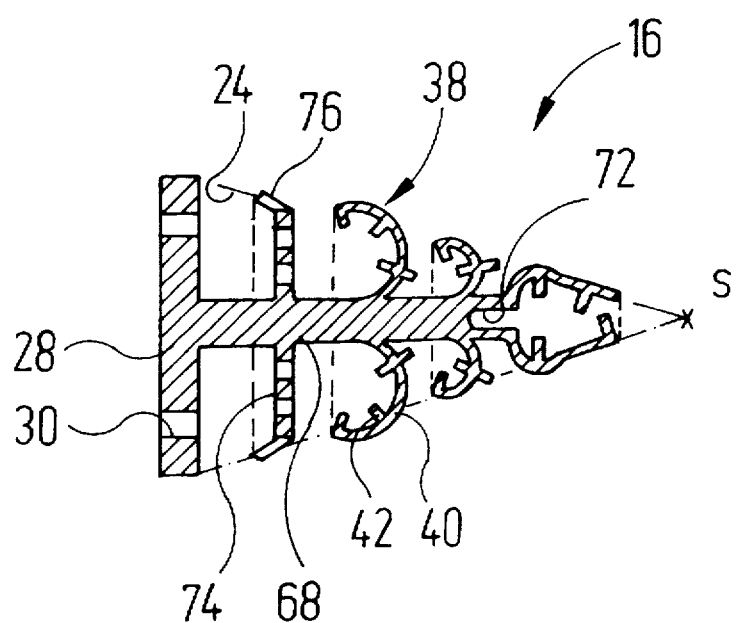
FIG. 3 is a longitudinal section through an anchoring unit for use in a further modified joint prothesis for small joints.

In the modified anchoring unit shown in FIG. 3 a central main anchoring element 68 of larger diameter, which is formed integral with the rear side of the mounting plate 28, has a plurality of groups of secondary anchoring elements 38 formed integral with its right hand portion as seen FIG. 3, the secondary anchoring elements each having arcuate shape. The angular extension of these arcs is about 200°. In those portions of the anchoring elements 38, which project beyond the cavity 24, the anchoring elements 38 are not provided with radially projecting portions of anchoring disks 42. The latter may be formed in these regions as semidisks or preferably as excentric disks extending in inward direction, only.

The anchoring elements 38 of a group lying in a common transversal plane are distributed in circumferential direction under same angular distance. The anchoring elements 38 of axially adjacent groups have been shown in the drawings as lying in same axial planes, for better clarity. In contrast thereto, in practical embodiments the anchoring elements 38 of adjacent groups are staggered in circumferential direction, preferably being offset by half a pitch in view of obtaining volumes filled with spongiosa being as uniform as possible.

Where anchoring elements 38 extend under small radial relative clearance (right end portion of the anchoring unit), the anchoring disks 42 are additionally axially staggered in view of not impeding radial elastic inward bending of the anchoring elements 38. Furthermore the end portion of the mounting stem 68 is formed with a slot 72, which also favours elastic inward bending of those of the anchoring elements 38 situated at the end of the mounting stem 68.

In the anchoring unit shown in FIG. 3 a large diameter anchoring disk 74 is provided in the immediate proximity of the mounting plate 28, the anchoring disk 74 again being formed formed with a large number of openings and thus having a grid type structure. Rim portions of the anchoring disk 74 are formed with radial slots 76 and these rim portions again are preferably arcuate, to facilitate conforming to the cavity provided in the bone and to facilitate insertion into the undersized cavity 24.

As may be seen from FIG. 3, the anchoring disks 74 and the anchoring elements 38 cooperate to form a cage structure, wherein ground spongiosa material will be retained so that the latter can be put into the cavity cut into the bone together with the anchoring unit.

The anchoring unit shown in FIG. 3 again is a one piece cast part made from titanium or a histocompatible alloy.

In the joint prosthesis shown in FIG. 4 components already described above have the same reference numerals fixed thereto, which have already been used in the preceeding text.

A cylindrical rolling contact element 78 is formed integral with the base plate 50 of the joint element 22. The cylindrical rolling surface of the rolling contact element 78 cooperates with a rolling contact surface 80 formed by the end face of the base plate 46 of the joint element 20.

The rolling contact element 78 is formed with a slot 82 being perpendicular to the rolling axis, which receives a shackle portion 84 under clearance conditions. The shackle portion 84 is formed integral with the base plate 46 of the prosthesis member 12. The shackle portion 84 has a shape similar to the shape of the end portion of a bone and defines a guiding slot having a slot portion 86 being perpendicular to the rolling contact surface 80 as well as a slot portion 88 being essentially transversal to the slot portion 86. The edges of the slot portions 86, 88 essentially correspond to an epicycloid.

A guide pin 90 carried by the rolling contact element 78 and being displaced from the axis of the rolling contact element 78 towards the rolling contact surface 80 moves in the slot portion 86, 88. The diameter of the guide pin 90 is somewhat smaller than the width of the slot portions 86, 88. The clearance of the guide pin in the slot arrangement measured in a direction being perpendicular to the rolling contact surface 80 is about 1.5 to 2 mm in the case of a finger joint.

When the prosthesis shown in FIG. 4 experiences compressive loads, the rolling contact element 78 will roll on the rolling contact surface 80 without slippage, the guide pin 90 following the edges of the slot portions 86, 88. When a slight tensional load is applied to the prosthesis of FIG. 1 or when large torsional loads are applied thereto together with small compressive loads, the circumferential surface of the rolling contact element 78 may also slip with respect to the rolling contact surface 80. Furthermore, under larger tensional loads of the joint the rolling contact element 78 may completely separate from the rolling contact surface 80 so that ready relative rotation of the prosthesis members 12, 14 with respect to the one another is warranted.

Once the joint has been implanted, the rolling contact element 78 is kept in engagement with the rolling contact surface 80 under the forces provided by the tendons and ligaments surrounding the joint.

In the prosthesis shown in FIG. 5 two bevelled base plates 46, 50 are arranged on the mounting plates 28 of the prosthesis members 12, 14, which are interconnected by a flex portion 92 formed integral therewith. If the flex portion 92 is rod shaped, the joint can be bent in arbitrary direction. If the cross section of the flex portion 92 taken in a plane being perpendicular to the plane of projection has a rectangular shape, one has an essentially uniaxial hinge joint.

In one embodiment, the anchoring disks are configured for contacting spongiosa which grows up to the anchoring disks after implantation and are adapted to achieve about 120% to about 140% of the compressional flow limit of the spongiosa upon exertion of short time working loads onto the spongiosa and to achieve about 60% to about 80% of the compressional flow limit of the spongiosa upon exertion of long time loads. Additionally, the anchoring elements comprise an overall surface area of from about 130% to about 270% of the wall surface of the bone cavity which is cut for implanting the prosthesis member.

We claim:

1. A joint prosthesis for insertion into a bone cavity of a small joint, comprising:

an anchoring unit and a joint element carried by the anchoring unit, the anchoring unit comprising a mounting plate and a plurality of spaced elongated anchoring elements extending away from the mounting plate and cooperating to define a generally frustoconical outer contour of the anchoring unit, each anchoring element being formed of a histocompatible alloy and comprising a plurality of radial anchoring disks axially spaced along its length and an end portion, the end portion being elastically deformable to automatically conform the anchoring unit to the geometry of the bone cavity when being inserted into the bone cavity.

2. The joint prosthesis of claim 1, wherein each anchoring element comprises a rod-shaped core and is individually connected to the mounting plate.

3. The joint prosthesis of claim 1, wherein the anchoring unit further comprises a stiffening element interconnecting adjacent anchoring elements in the vicinity of the anchoring plate, the stiffening element including a plurality of axially spaced radial anchoring disks.

4. The joint prosthesis of claim 1, wherein one of the anchoring elements is essentially centrally arranged on the mounting plate, the anchoring disks in the vicinity of said mounting plate have a diameter comparable to the diameter of the mounting plate, the anchoring disks have progressively decreasing diameters toward the free end of the anchoring element and the anchoring disks at the end portion of said anchoring element comprise an axial slot.

5. The joint prosthesis of claim 4, wherein the anchoring disks comprise a grid structure.

6. The joint prosthesis of claim 4, wherein the anchoring disks comprise radially outwardly extending portions having slots and being deformable in a radial direction.

7. The joint prosthesis of claim 1, wherein said unit comprises a first anchoring element coupled to an essentially central portion of the mounting plate; and secondary anchoring elements connected to the first anchoring element and being elastically deformable at their end portions, the axially spaced anchoring disks of the secondary anchoring elements having a diameter less than the diameter of the mounting plate.

8. The joint prosthesis of claim 7, wherein the secondary anchoring elements are essentially arcuate in shape.

9. The joint prosthesis of claim 8, wherein the secondary anchoring elements each comprise a circumferential extension greater than 180°.

10. The joint prosthesis of claim 9, wherein the circumferential extension of each secondary anchoring element is less than about 225°.

11. The joint prosthesis of claim 10, wherein the arcuate shape comprises an open portion facing the mounting plate.

12. The joint prosthesis of claim 7, wherein the anchoring unit comprises axially spaced groups of the secondary anchoring elements, the anchoring elements of each group being arranged in a common radial plane, equally spaced in a circumferential direction.

13. The joint prosthesis of claim 12, wherein the secondary anchoring elements of axially adjacent groups are arranged under the same angular pitch and are staggered in a circumferential direction by half of the angular pitch.

14. The joint prosthesis of claim 1, wherein the anchoring elements are adapted to project beyond the desired contour of the bone cavity in a free state.

15. The joint prosthesis of claim 14, wherein the anchoring elements each comprise a convex contact surface adapted to extend beyond the desired contour of the bone cavity in a free state.

16. The joint prosthesis of claim 15, wherein the convex contact surface of each anchoring element comprises contact members formed integrally with the anchoring elements and radially projecting beyond the anchoring disks.

17. The joint prosthesis of claim 11, wherein the secondary anchoring elements each comprise a convex contact surface adapted to extend beyond the desired contour of the bone in a free state, and further wherein the contact surface is formed by portions of the arcuate secondary anchoring elements which are free of outwardly projecting radial anchoring disks.

18. The joint prosthesis of claim 17, wherein the arcuate secondary anchoring element portions forming the contact surface carry radially inwardly projecting anchoring disks of a semi-circular or an excentric circular shape.

19. The joint prosthesis of claim 1, wherein the anchoring disks are configured for contacting spongiosa after implantation and for achieving about 120% to about 140% of a compressional flow limit of the spongiosa upon exertion of short time working loads onto the spongiosa, and for achieving about 60% to about 80% of the compressional flow limit of the spongiosa upon exertion of long time loads onto the spongiosa.

20. The joint prosthesis of claim 18, wherein the anchoring element comprises an overall surface area of from about 130% to about 270% of the wall surface of the bone cavity.

21. The joint prosthesis of claim 1, wherein each anchoring element comprises a core having a diameter from about 0.8 to 2.0 mm.

22. The joint prosthesis of claim 6, wherein the anchoring disks have a diameter from about 0.6 to 1.2 mm greater than the diameter of the core.

23. The joint prosthesis of claim 1, wherein the anchoring disks have an axial length from about 0.5 to 1.0 mm.

24. The joint prosthesis of claim 1, wherein a distance between adjacent anchoring disks is from about 2.0 to 4.0 mm.

25. The joint prosthesis of claim 1, wherein each anchoring element comprises a core having a diameter of from about 0.8 to 2.0 mm, the anchoring disks have a diameter of from about 0.6 to 1.2 mm greater than the core diameter and an axial length of from about 0.5 to 1.0 mm, and the distance between adjacent anchoring disks is from about 2.0 to 4.0 mm.

26. The joint prosthesis of claim 1, wherein the histocompatible alloy comprises titanium.

27. A joint prosthesis for insertion into a bone cavity of a small joint, comprising:

an anchoring unit and a joint element carried by the anchoring unit, the anchoring unit comprising a mounting plate and a plurality of spaced elongated anchoring elements extending away from the mounting plate and cooperating to define a generally frustoconical outer contour of the anchoring unit, each anchoring element being formed of titanium and comprising a plurality of radial anchoring disks axially spaced along its length and an end portion, the end portion being elastically deformable to automatically conform the anchoring unit to the geometry of the bone cavity when being inserted into the bone cavity.

28. A joint prosthesis for insertion into a bone cavity of a small joint, comprising;

two prosthesis members, each prosthesis member having an anchoring unit and a joint member carried by the anchoring unit, each anchoring unit comprising a mounting plate and a plurality of spaced elongated anchoring elements extending away from the mounting plate and cooperating to define a generally frustoconical outer contour of the anchoring unit, and each anchoring element being formed of a histocompatible alloy and comprising a plurality of radial anchoring disks axially spaced along its length and an end portion, the end portion being elastically deformable to automatically conform the anchoring unit to the geometry of the bone cavity when being inserted into the bone cavity.

29. The joint prosthesis of claim 28, wherein said joint members are formed of a histocompatible thermoplastic material.

30. The joint prosthesis of claim 29, wherein said histocompatible thermoplastic material comprises polyethylene.

31. The joint prosthesis of claim 23, wherein the anchoring element is formed of titanium.

32. The joint prosthesis of claim 30, wherein the joint members each comprise at least one mounting pin on a rear side thereof, which pin is fixed in an opening of the mounting plate by positive engagement or thermal riveting.

33. The joint prosthesis of claim 28, wherein one of the joint members comprises a spherical joint socket, and the other of the joint members comprises a spherical joint ball having an abutment disk and adapted for engaging the first joint member upon a predetermined amount of relative tilting movement of the joint members.

34. The joint prosthesis of claim 33, wherein the abutment disk comprises an elastically deformable rim portion that radially projects in a cantilever manner.

35. The joint prosthesis of claim 34, wherein said rim portion is provided with radial slots.

36. The joint prosthesis of claim 28, wherein one of the members comprises a cylindrical joint socket, and the other of the joint members comprises a cylindrical joint ball adapted to be coupled to the cylindrical joint socket through a connection formed by a pin and an elongated opening to form an essentially uniaxial cylinder joint.

37. The joint prosthesis of claim 36, wherein the connection allows movement in a direction perpendicular to a main plane of movement of the cylinder joint.

38. The joint prosthesis of claim 32, wherein one of the joint members comprises a cylindrical rolling contact element and the other of the joint members comprises an essentially flat rolling contact surface, and the joint prosthesis further comprises guide means allowing for lifting the rolling contact element off of the rolling contact surface upon tension loads being exerted on the joint prosthesis, for rolling the rolling contact element on the rolling contact surface under compressional loads of the joint prosthesis, and for slippage of the rolling contact element with respect to the rolling contact surface upon the joint prosthesis experiencing a tension load which is small as compared to an applied torque.

39. The joint prosthesis of claim 38, wherein said guide means comprises a guide pin extending parallel to the rolling contact surface and being carried by one of the prosthesis members, a contoured guiding slot arranged on the other prosthesis member, the slot lying in a plane perpendicular to the rolling contact surface and having a first slot portion adjacent the rolling contact surface and into which the guide pin is adapted for movement under clearance conditions when tension loads are exerted on the joint prosthesis, and having a second slot portion enlarged in accordance with the rolling movement and into which the guide pin is adapted for movement under clearance condition when the rolling contact element rolls on the rolling contact surface.

40. A joint prosthesis for insertion into a bone cavity of a small joint, comprising;

two prosthesis members, each prosthesis member having an anchoring unit and a joint member carried by the anchoring unit, each anchoring unit comprising a mounting plate and a plurality of spaced elongated anchoring elements extending away from the mounting plate and cooperating to define a generally frustoconical outer contour of the anchoring unit, and each anchoring element being formed of titanium and comprising a plurality of radial anchoring disks axially spaced along its length and an end portion, the end portion being elastically deformable to automatically conform the anchoring unit to the geometry of the bone cavity when being inserted into the bone cavity.

41. A joint prosthesis, comprising a first joint member comprising a cylindrical joint socket and a second joint member comprising a cylindrical joint ball adapted to be coupled to the cylindrical joint socket by a connection comprising a pin and an elongated opening to form an essentially uniaxially cylinder joint, the connection allowing movement in a direction perpendicular to the main plane of movement of the cylinder joint, each joint member being carried by an anchoring unit, each anchoring unit comprising a mounting plate and a plurality of spaced elongated anchoring elements extending away from the mounting plate and cooperating to define a generally frustoconical outer contour of the anchoring unit, and each anchoring element being formed of a histocompatible alloy and comprising a plurality of radial anchoring disks axially spaced along its length and an end portion, the end portion being elastically deformable to automatically conform the anchoring unit to the geometry of the bone cavity when being inserted into the bone cavity.

* * * * *